US011058861B2

(12) United States Patent
Pak et al.

(10) Patent No.: US 11,058,861 B2
(45) Date of Patent: Jul. 13, 2021

(54) LOCKING MECHANISM FOR ROLLER CLAMP

(71) Applicant: CareFusion 303, Inc., San Diego, CA (US)

(72) Inventors: Janice Pak, Centennial, CO (US); Wesley Underwood, La Habra, CA (US); Shawn DeKalb, San Diego, CA (US)

(73) Assignee: CAREFUSION 303, INC., San Diego, CA (US)

( * ) Notice: Subject to any disclaimer, the term of this patent is extended or adjusted under 35 U.S.C. 154(b) by 17 days.

(21) Appl. No.: 16/379,639

(22) Filed: Apr. 9, 2019

(65) Prior Publication Data
US 2020/0324103 A1    Oct. 15, 2020

(51) Int. Cl.
*F16K 7/06* (2006.01)
*A61M 39/28* (2006.01)

(52) U.S. Cl.
CPC .............. *A61M 39/286* (2013.01); *F16K 7/06* (2013.01); *A61M 2205/276* (2013.01)

(58) Field of Classification Search
CPC ................ A61M 39/28; A61M 39/286; A61M 2205/276; A61M 5/16877; F16K 7/066; F16K 7/06; F16K 35/06
USPC ........................................................... 251/6
See application file for complete search history.

(56) References Cited

U.S. PATENT DOCUMENTS

| 2,595,511 | A | * | 5/1952 | Butler | A61M 39/286 |
| | | | | | 251/6 |
| 3,099,429 | A | * | 7/1963 | Broman | A61M 39/286 |
| | | | | | 251/6 |
| 3,900,184 | A | * | 8/1975 | Burke | A61M 39/286 |
| | | | | | 251/6 |

(Continued)

FOREIGN PATENT DOCUMENTS

| DE | 9214852 | 12/1993 |
| EP | 2105160 A1 * | 9/2009 ............ A61M 39/286 |

(Continued)

OTHER PUBLICATIONS

International Search Report and Written Opinion for Application No. PCT/US2020/027104, dated Jun. 10, 2020, 14 pages.

*Primary Examiner* — Umashankar Venkatesan
(74) *Attorney, Agent, or Firm* — Morgan, Lewis & Bockius LLP

(57) ABSTRACT

Roller clamps are described herein. A roller clamp includes a housing, a roller wheel, and a locking device. The housing includes a first wall and a second wall, wherein the first wall and the second wall are spaced apart to define a longitudinal channel therebetween, the housing including an upper opening and a lower opening configured to allow a tubing to pass through the longitudinal channel. The roller wheel is disposed at least partially within the longitudinal channel and configured to engage the tubing, the roller wheel including a plurality of teeth extending from an outer surface of the roller wheel, wherein a longitudinal position of the roller wheel relative to the channel adjusts a flow rate through the tubing. The locking device is releasably engaged to the housing and the roller wheel, wherein the locking device prevents movement of the roller wheel from the longitudinal position.

12 Claims, 5 Drawing Sheets

(56) References Cited

U.S. PATENT DOCUMENTS

| | | | | | |
|---|---|---|---|---|---|
| 3,918,675 | A | * | 11/1975 | Forberg | A61M 39/28 |
| | | | | | 251/6 |
| 4,285,492 | A | * | 8/1981 | Bujan | A61M 39/286 |
| | | | | | 251/6 |
| 4,406,440 | A | * | 9/1983 | Kulle | A61M 39/286 |
| | | | | | 251/6 |
| 6,341,757 | B1 | | 1/2002 | Starchevich | |
| 2009/0254034 | A1 | * | 10/2009 | Beck | A61M 39/284 |
| | | | | | 604/118 |

FOREIGN PATENT DOCUMENTS

| | | | | |
|---|---|---|---|---|
| FR | 1327140 | | 5/1963 | |
| GB | 1322546 | | 7/1973 | |
| JP | H-0648676 | * | 5/1994 | A61M 5/168 |

* cited by examiner

LOCKING MECHANISM FOR ROLLER CLAMP

FIELD OF THE INVENTION

The present disclosure generally relates to roller clamps, and, in particular, to roller clamps with locking mechanisms.

BACKGROUND

Medical treatments often include the infusion of a medical fluid (e.g., a saline solution or a liquid medication) to patients using an intravenous (IV) catheter that is connected though an arrangement of flexible tubing and fittings, commonly referred to as an "IV set," to a source of fluid, for example, an IV bag. Often, the flow rate through the tubing is adjusted to control the rate of infusion for the patient. Devices to adjust the flow rate through the tubing may not be locked at a desired flow rate.

Therefore, in some applications, the rate of infusion may be changed inadvertently or by unauthorized personnel.

SUMMARY

The disclosed subject matter relates to roller clamps with locking mechanisms. In certain embodiments, a roller clamps is disclosed that comprises a housing comprising a first wall and a second wall, wherein the first wall and the second wall are spaced apart to define a longitudinal channel therebetween, the housing including an upper opening and a lower opening configured to allow a tubing to pass through the longitudinal channel; a roller wheel disposed at least partially within the longitudinal channel and configured to engage the tubing, the roller wheel including a plurality of teeth extending from an outer surface of the roller wheel, wherein a longitudinal position of the roller wheel relative to the channel adjusts a flow rate through the tubing; and a locking device releasably engaged to the housing and the roller wheel, wherein the locking device prevents movement of the roller wheel from the longitudinal position.

In certain embodiments, a roller clamp is disclosed that comprises a housing comprising a first wall and a second wall, wherein the first wall and the second wall are spaced apart to define a longitudinal channel therebetween, the housing including an upper opening and a lower opening configured to allow a tubing to pass through the longitudinal channel; a roller wheel disposed at least partially within the longitudinal channel and configured to engage the tubing, the roller wheel including a plurality of teeth extending from an outer surface of the roller wheel, wherein a longitudinal position of the roller wheel relative to the channel adjusts a flow rate through the tubing; and an access door coupled to the housing, the access door comprising a plurality of mating teeth, wherein the plurality of mating teeth are configured to engage with at least one of the plurality of teeth of the roller wheel to prevent movement of the roller wheel when the access door is in a closed position.

In certain embodiments, a method for adjusting a flow rate through a tubing is disclosed that comprises providing the tubing through a roller clamp; adjusting a longitudinal position of a roller wheel of the roller clamp to adjust the flow rate through the tubing; and covering the roller wheel with a locking device engaged to a housing of the roller clamp.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

Figure 1:
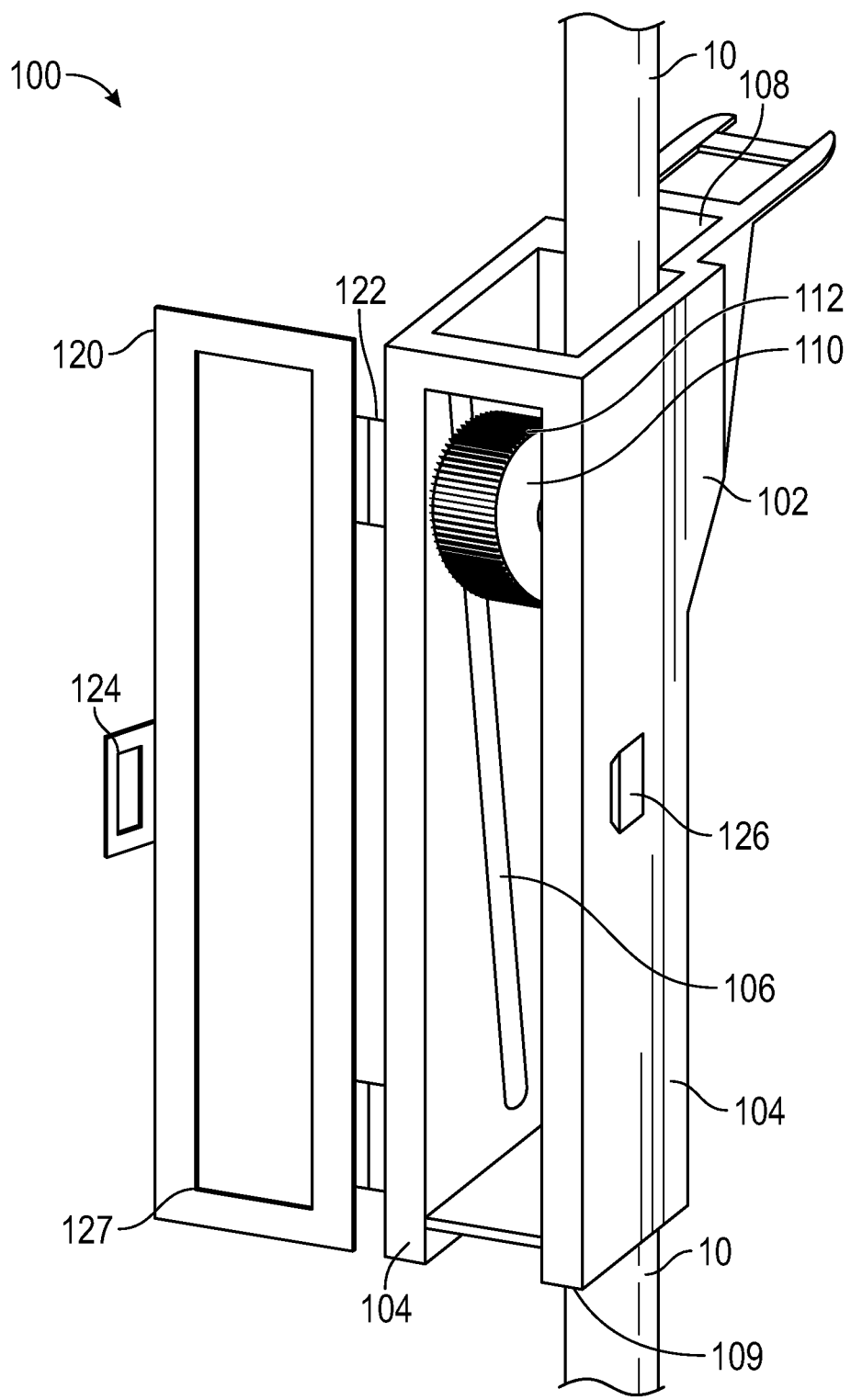
FIG. 1 is a perspective view of a roller clamp, in accordance with various aspects of the present disclosure.

The disclosed roller clamp incorporates a housing, a roller wheel, and a locking device. The locking device can releasably engage the housing and the roller wheel to prevent unintended or unauthorized movement of the roller wheel. By preventing unintended or unauthorized movement of the roller wheel, the flow rate for infusion can be controlled without unexpected drifts or changes in the infusion rate.

The detailed description set forth below is intended as a description of various configurations of the subject technology and is not intended to represent the only configurations in which the subject technology may be practiced. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding. Reference numbers may have letter suffixes appended to indicate separate instances of a common element while being referred to generically by the same number without a suffix letter.

While the following description is directed to controlling and maintaining a flow rate during the administration of medical fluid using the disclosed roller clamp, it is to be understood that this description is only an example of usage and does not limit the scope of the claims. Various aspects of the disclosed roller clamp may be used in any application where it is desirable to control a fluid flow rate without permitting unintended or unauthorized changes to the flow rate.

The disclosed roller clamp overcomes several challenges discovered with respect to certain conventional roller clamps. One challenge with certain conventional roller clamps is that roller clamps may be inadvertently adjusted by incidental contact from patients and/or clinicians. Further, roller clamps may be intentionally adjusted by unauthorized personnel, including patients. Because the inadvertent or the unauthorized adjustment of roller clamps can alter the flow rate of the administered medical fluid, thereby compromising the effects of the infusion therapy or harming the patient, the use of conventional roller clamps is undesirable.

Therefore, in accordance with the present disclosure, it is advantageous to provide a roller clamp as described herein that eliminates or substantially reduces potential accidental or unauthorized adjustment of the roller clamp. The disclosed roller clamp provides a locking device that permits the authorized adjustment of the flow rate of an administered medical fluid while preventing inadvertent or unauthorized adjustment of the flow rate.

An example of a roller clamp that prevents inadvertent or unauthorized adjustment of the medical fluid flow rate is now described.

FIG. 1 is a perspective view of a roller clamp 100, in accordance with various aspects of the present disclosure. In the depicted example, the roller clamp 100 can control the rate of fluid flow through tubing 10.

In some applications, the tubing 10 can carry medical fluid from a fluid source, such as an IV bag, to a patient during the administration or infusion of medical fluids. As illustrated, the tubing 10 can pass through the roller clamp 100.

For example, the tubing 10 can pass through an upper opening 108 of the housing 102, extend along the longitudinal length of the channel 106 and exit the roller clamp 100 through a lower opening 109. During operation, a clinician can adjust the roller clamp 100 to control the rate of fluid flow through the tubing 10 by selectively varying the amount of compression or crimping force on the portion of tubing 10 disposed within the channel 106 of the roller clamp 100, which can vary the cross-sectional profile of the tubing 10.

In some applications, a roller wheel 110 can be moved and/or rotated within the longitudinal channel 106 to adjust the amount of compression or crimping force exerted on the tubing 10, adjusting the flow rate through the tubing 10. In the depicted example, the roller wheel 110 is movable along one or more ramped or sloped tracks or guides formed in the walls 104 of the housing 102. In some embodiments, the roller wheel 110 includes one or more teeth or grooves 112 to facilitate engagement.

Therefore, during operation, as the roller wheel 110 is moved longitudinally within the longitudinal channel 106, the amount of compression force exerted upon the tubing 10 can be increased or decreased by altering the longitudinal position of the roller wheel 110 relative to the housing 102. For example, when a clinician moves the roller wheel 110 toward the lower opening 109 of the housing 102, the roller wheel 110 may increase the compression or crimping force on the tubing 10, decreasing the fluid flow through the tubing 10. Optionally, when the roller wheel 110 is disposed at a lowermost position, the roller wheel 110 may fully compress or crimp the tubing 10, preventing any fluid flow through the tubing 10. Similarly, when the roller wheel 110 is moved toward the upper opening 108 of the housing 102, the roller wheel 110 may decrease the compression or crimping force on the tubing 10, increasing the fluid flow through the tubing 10. Optionally, when the roller wheel 110 is disposed at an uppermost position, the roller wheel 110 may not impart any compression or crimping force on the tubing 10. As can be appreciated, the relationship between the longitudinal position of the roller wheel 110 and the amount of compression force exerted upon the tubing 10 can deviate from the example described above. For example, the amount of compression force exerted upon the tubing 10 may increase or decrease as the roller wheel 110 is moved or rotated upward or downward, or towards a desired position along the longitudinal channel 106.

Therefore, during operation, a clinician can adjust the longitudinal position of the roller wheel 110 to adjust the flow rate through the tubing 10. However, the longitudinal position of the roller wheel 110, and therefore the flow rate through the tubing 10 may be inadvertently adjusted by accidental contact or adjusted by unauthorized personnel.

As illustrated, the roller clamp 100 can include a locking device to prevent inadvertent or unauthorized adjustment of the longitudinal position of the roller wheel 110. In some embodiments, the locking device can engage the roller wheel 110 and/or the housing 102 to prevent movement of the roller wheel 110 relative to the housing. In some embodiments, the locking device can cover or encase the roller wheel 110 to prevent and/or discourage unauthorized access to the roller wheel 110.

For example, the roller clamp 100 can include an access door 120 to encase the roller wheel 110 and prevent inadvertent and/or unauthorized adjustment of the roller wheel 110. After setting the flow rate of the tubing 10 with the roller clamp 100, the access door 120 can be moved to a closed position to encase the roller wheel 110. Optionally, the access door 120 can have a latch 124 that engages to a latching feature 126 of the wall 104 of the housing 102. The latch 124 can be a snap mechanism in snap engagement with the latching feature 126. Similarly, the access door 120 can be opened by a clinician to adjust the roller clamp 100.

In some embodiments, the access door 120 is attached to the housing 102 via hinges 122. The hinges 122 can be formed as living hinges to simplify manufacturing.

Optionally, the access door 120 can include a recessed portion 127 to allow the access door 120 to be closed without contacting the roller wheel 110. Advantageously, in some applications, the recessed portion 127 allows for the access door 120 to be closed without changing the amount of compression force exerted upon the tubing 10 by the roller wheel 110.

Figure 2:
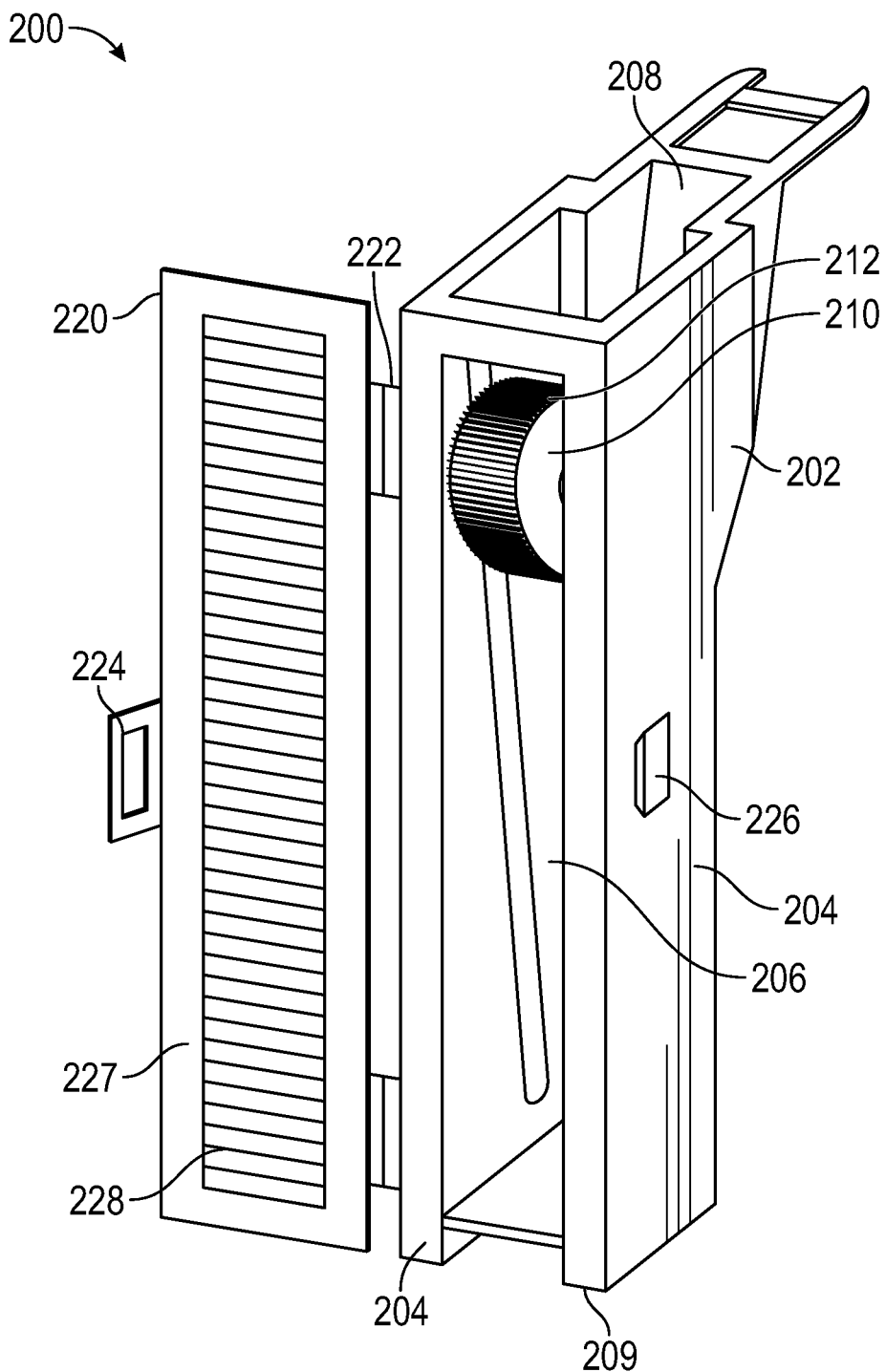
FIG. 2 is a perspective view of a roller clamp, in accordance with various aspects of the present disclosure.

FIG. 2 is a perspective view of a roller clamp 200, in accordance with various aspects of the present disclosure. In the illustrated embodiment, the roller clamp 200 includes features that are similar to features previously discussed with respect to roller clamp 100. Except where noted, similar features may be referred to with similar reference numerals and may reference corresponding descriptions.

In some embodiments, the access door 220 can include mating teeth 228 to engage or interlock with the grooves 212 of the roller wheel 210 in a closed position to retain the roller wheel 210 in the set longitudinal position. In a closed position, one or more mating teeth 228 can mesh with one or more grooves 212 of the roller wheel 210 to prevent longitudinal and/or rotational movement of the roller wheel 210, further preventing inadvertent and/or unauthorized adjustment of the roller wheel 210.

Figure 3:
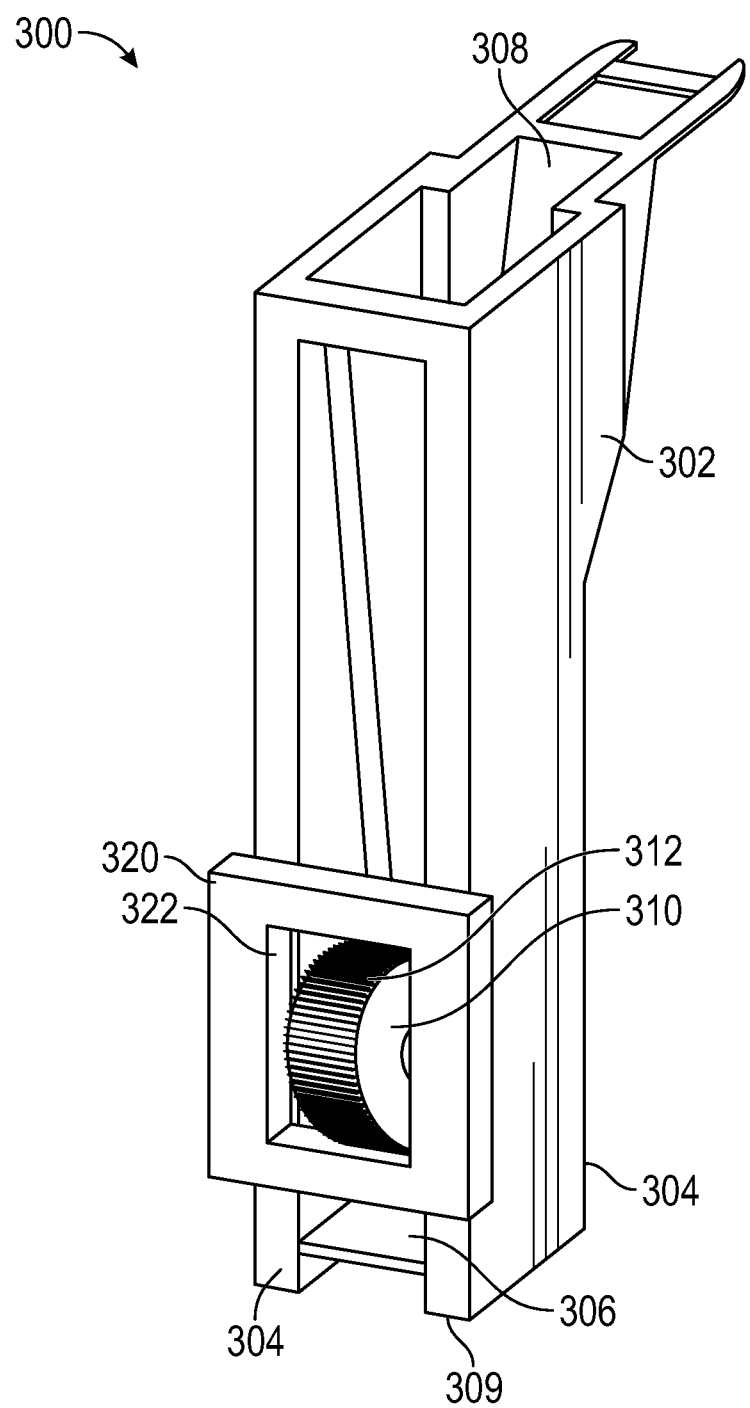
FIG. 3 is a perspective view of a roller clamp, in accordance with various aspects of the present disclosure.

FIG. 3 is a perspective view of a roller clamp 300, in accordance with various aspects of the present disclosure. In the illustrated embodiment, the roller clamp 300 includes features that are similar to features previously discussed with respect to roller clamp 100. Except where noted, similar features may be referred to with similar reference numerals and may reference corresponding descriptions.

As illustrated, the roller clamp 300 includes a locking tab 320 to allow a clinician to adjust and lock the roller wheel 310 to prevent inadvertent and/or unauthorized adjustment of the roller wheel 310. The locking tab 320 is disposed around the roller wheel 310 and is configured to slide longitudinally along the housing 302 when in an unlocked position.

During operation, the clinician can access the roller wheel 310 through the window 322 of the locking tab 320. In an unlocked position, the clinician can move the roller wheel 310 and the surrounding locking tab 320 to the desired longitudinal position to provide a desired fluid flow rate.

After setting the flow rate of the tubing with the roller clamp 300, the locking tab 320 can be moved to a locked position to prevent longitudinal movement of the roller wheel 310. In some embodiments, a clinician or other use can push the locking tab 320 into the housing 302 to lock the position of the roller wheel 310. Optionally, the locking tab 320 can be pulled to be moved into the locked position. In some embodiment, the locking tab 320 can engage one or more detents formed in the housing 302 in the locked position to prevent the locking tab 320 and the roller wheel 310 from moving longitudinally. Similarly, the locking tab 320 can be disengaged from the housing 302 to allow the clinician to adjust the roller wheel 310.

Figure 4C:
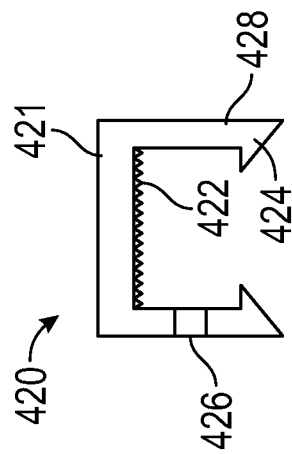
FIG. 4C is a cross-sectional view of an immobilizer for use with the roller clamp of FIG. 4A, in accordance with various aspects of the present disclosure.
Figure 4B:
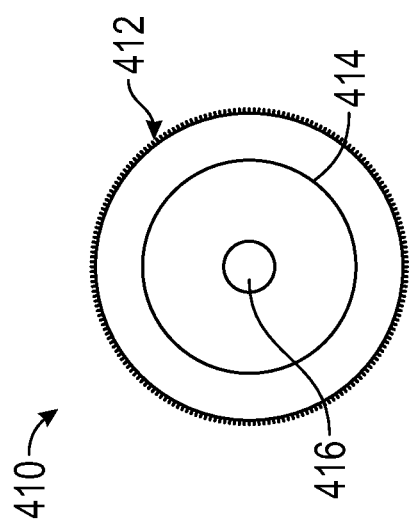
FIG. 4B is a side view of a roller wheel for use with the roller clamp of FIG. 4A, in accordance with various aspects of the present disclosure.
Figure 4A:
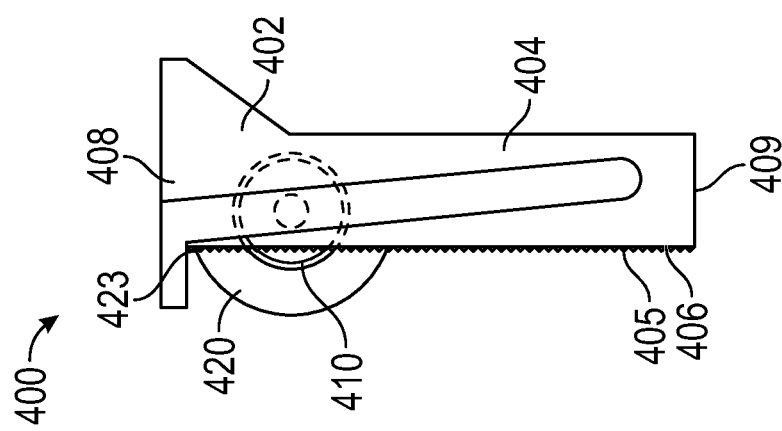
FIG. 4A is a side view of a roller clamp, in accordance with various aspects of the present disclosure.

FIG. 4A is a side view of a roller clamp 400, in accordance with various aspects of the present disclosure. In the illustrated embodiment, the roller clamp 400 includes features that are similar to features previously discussed with respect to roller clamp 100. Except where noted, similar features may be referred to with similar reference numerals and may reference corresponding descriptions.

As illustrated, the roller clamp 400 includes an immobilizer 420 to allow a clinician to adjust and lock the roller wheel 410 to prevent inadvertent and/or unauthorized adjustment of the roller wheel 410. Prior to installation of the immobilizer 420, the clinician can move the roller wheel 410 to a desired longitudinal position to provide a desired fluid flow rate.

After setting the flow rate of the tubing with the roller clamp 400, the immobilizer 420 can be installed to engage the roller wheel 410 and the housing 402. FIG. 4B is a side view of a roller wheel 410 for use with the roller clamp 400 of FIG. 4A, in accordance with various aspects of the present disclosure. FIG. 4C is a cross-sectional view of an immobilizer 420 for use with the roller clamp 400 of FIG. 4A, in accordance with various aspects of the present disclosure. With reference to FIGS. 4A-4C, the immobilizer 420 can be engaged to the housing 402 and the roller wheel 410 to prevent movement of the roller wheel 410.

As illustrated, the immobilizer 420 can partially encase the exposed portion of the roller wheel 410. In some embodiments, the immobilizer 420 can have a semi-circular profile that is complimentary to the profile of the roller wheel 410. In some embodiments, the curved surface 421 of the immobilizer 420 can include one or more locking teeth 422 to engage the grooves 412 of the roller wheel 410.

In some embodiments, the housing 402 can include housing teeth 405 that extend from the housing 402 adjacent to the longitudinal channel 406. Optionally, the immobilizer 420 can further include secondary locking teeth 423 to engage housing teeth 405 extending from the housing 402. As illustrated, the engagement of the locking teeth 422 and/or the locking teeth 423 can lock the roller wheel 410 to the housing 402 to prevent longitudinal movement of the roller wheel 410 and prevent unauthorized access to the roller wheel.

Further, to retain the immobilizer 420 to the roller clamp 400, walls 428 can extend over an axial lip 414 of the roller wheel 410 to permit retainers 424 to engage an edge of the axial lip 414 of the roller wheel 410, preventing axial movement of the immobilizer 420 and keeping the locking teeth 422 and locking teeth 423 in engagement. In some embodiments, the walls 428 and/or the retainers 424 of the immobilizer 420 can resiliently deform to allow the immobilizer 420 to snap fit over the axial lip 414 of the roller wheel 410.

Optionally, to facilitate removal, a wall 428 of the immobilizer 420 can include a keyway 426 to permit the insertion of a key to disengage the retainer 424 from the roller wheel 410. Upon insertion of the key, the wall 428 can be resiliently deformed to disengage the retainer 424 from the roller wheel 410. In some embodiments, the keyway 426 can be shaped or keyed to only permit a complimentary key to remove the immobilizer 420. Upon removal of the immobilizer 420, the clinician can adjust the roller wheel 410 as needed.

Figure 5:
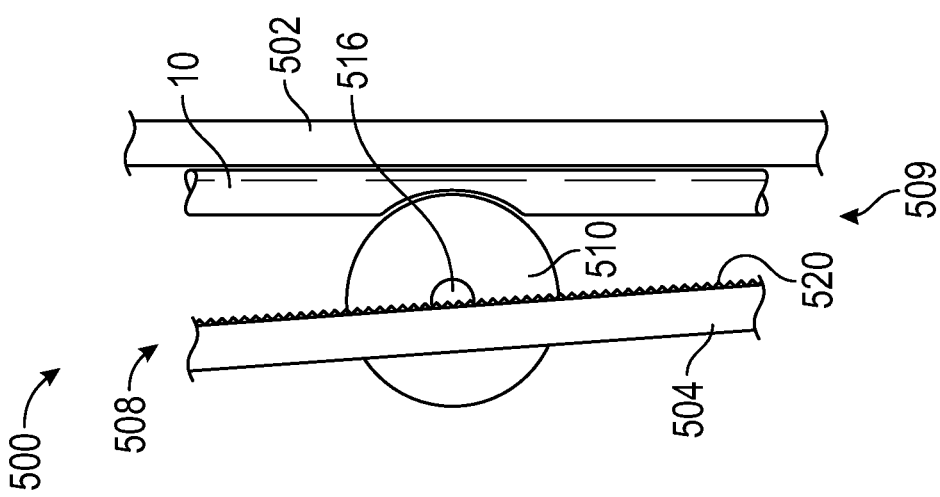
FIG. 5 is a partial cross-sectional view of a roller clamp, in accordance with various aspects of the present disclosure.

FIG. 5 is a partial cross-sectional view of a roller clamp, in accordance with various aspects of the present disclosure. In the illustrated embodiment, the roller clamp 500 includes features that are similar to features previously discussed with respect to roller clamp 100. Except where noted, similar features may be referred to with similar reference numerals and may reference corresponding descriptions.

As illustrated, the roller clamp 500 includes locking teeth 520 to allow a clinician to adjust and lock the roller wheel 510 to prevent inadvertent and/or unauthorized adjustment of the roller wheel 510. In the depicted example, the locking teeth 520 extend from a wall 504 of the housing 502. In some embodiments, the housing 502 can include locking teeth 520 extending from both walls 504 of the housing 502.

During operation, the clinician can depress the roller wheel 510 to disengage the pin 516 from the locking teeth 520. Once disengaged, the clinician can move the roller wheel 510 to the desired longitudinal position to provide the desired fluid flow rate.

After setting the flow rate of the tubing 10 with the roller clamp 500, the roller wheel 510 can be released, engaging the pin 516 between two of the locking teeth 520, preventing the roller wheel 510 from moving longitudinally. In some embodiments, the pin 516 can be frictionally engaged with the locking teeth 520.

Figure 6:
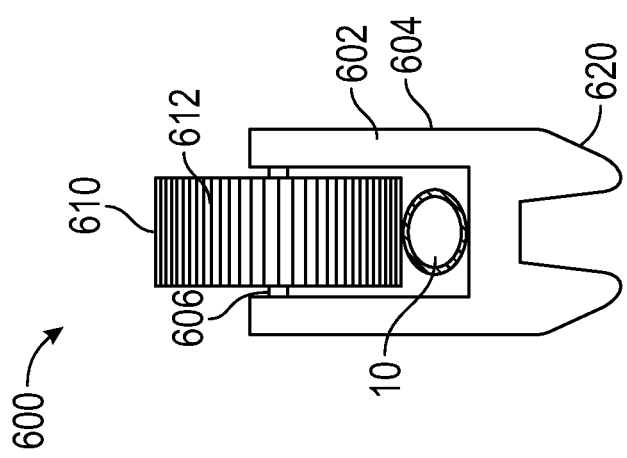
FIG. 6 is a partial cross-sectional view of a roller clamp, in accordance with various aspects of the present disclosure.

FIG. 6 is a partial cross-sectional view of a roller clamp 600, in accordance with various aspects of the present disclosure. In the illustrated embodiment, the roller clamp 600 includes features that are similar to features previously discussed with respect to roller clamp 100. Except where noted, similar features may be referred to with similar reference numerals and may reference corresponding descriptions.

As illustrated, the roller clamp 600 includes resiliently biased walls 604 to allow a clinician to adjust and lock the roller wheel 610 to prevent inadvertent and/or unauthorized adjustment of the roller wheel 610. In the depicted example, the wall extensions 620 extend from each respective wall 604 to allow a clinician to urge the walls 604 apart. The walls 604 can be resiliently coupled together and biased to contact the roller wheel 610.

During operation, the clinician can squeeze or compress the wall extensions 620 toward each other to urge the walls 604 apart to disengage the walls 604 from the roller wheel 610. While the walls 604 are urged apart, the clinician can move the roller wheel 610 to the desired longitudinal position to provide the desired fluid flow rate.

After setting the flow rate of the tubing 10 with the roller clamp 600, the wall extensions 620 can be released, allowing the biased walls 604 to engage the roller wheel 610, preventing the roller wheel 610 from moving longitudinally.

Figure 7:
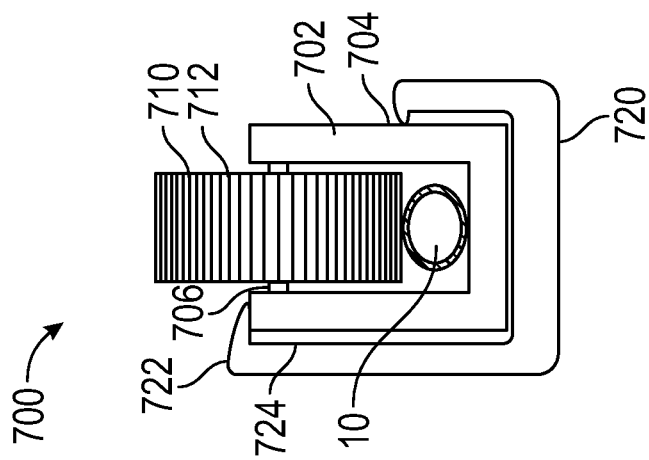
FIG. 7 is a partial cross-sectional view of a roller clamp, in accordance with various aspects of the present disclosure.

FIG. 7 is a partial cross-sectional view of a roller clamp 700, in accordance with various aspects of the present disclosure. In the illustrated embodiment, the roller clamp 700 includes features that are similar to features previously discussed with respect to roller clamp 100. Except where noted, similar features may be referred to with similar reference numerals and may reference corresponding descriptions.

As illustrated, the roller clamp 700 includes a slider 720 to allow a clinician to adjust and lock the roller wheel 710 to prevent inadvertent and/or unauthorized adjustment of the roller wheel 610. In the depicted example, the slider 720 includes a biasing arm 724 that extends to urge the roller wheel 710 toward the wall 704 of the housing.

During operation, the clinician can disengage the biasing arm 724 from the roller wheel 710 by deflecting the biasing arm 724 away from the roller wheel 710. Alternatively, the clinician can slide the slider 720 away from the roller wheel 710. After disengaging the biasing arm 724 from the roller wheel 710, the clinician can move the roller wheel 710 to the desired longitudinal position to provide the desired fluid flow rate.

After setting the flow rate of the tubing 10 with the roller wheel 710, the biasing arm 724 can be released to engage the roller wheel 710, or alternatively the slider 720 can be aligned to engage the biasing arm 724 against the roller wheel 710, preventing the roller wheel 610 from moving longitudinally.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A roller clamp, comprising:
a housing comprising a first wall and a second wall, wherein the first wall and the second wall are spaced apart to define a longitudinal channel therebetween, the housing including an upper opening and a lower opening configured to allow a tubing to pass through the longitudinal channel;
a roller wheel disposed at least partially within the longitudinal channel and configured to engage the tubing, the roller wheel including a plurality of teeth extending from an outer surface of the roller wheel, wherein a longitudinal position of the roller wheel relative to the channel adjusts a flow rate through the tubing; and
an access door coupled to the housing, the access door comprising a plurality of mating teeth, wherein the plurality of mating teeth is configured to engage with at least one of the plurality of teeth of the roller wheel to prevent movement of the roller wheel when the access door is in a closed position.

2. The roller clamp of claim 1, wherein the access door comprises a latch releasably coupling the access door to the housing.

3. The roller clamp of claim 2, wherein the latch comprises a snap mechanism.

4. A method for adjusting a flow rate through a tubing, the method comprising:
providing the tubing through a roller clamp;
adjusting a longitudinal position of a roller wheel of the roller clamp to adjust the flow rate through the tubing, wherein the roller wheel includes a plurality of teeth extending from an outer surface of the roller wheel;
covering the roller wheel with a locking device engaged to a housing of the roller clamp; and
engaging a plurality of mating teeth of the locking device with at least one of the plurality of teeth of the roller wheel to prevent movement of the roller wheel when the locking device is in a closed position.

5. The method of claim 4, further comprising:
engaging the roller wheel with the locking device to releasably couple the roller wheel to the housing to prevent movement of the roller wheel.

6. A roller clamp, comprising:
a housing comprising a first wall and a second wall, wherein the first wall and the second wall are spaced apart to define a longitudinal channel therebetween, the housing including an upper opening and a lower opening configured to allow a tubing to pass through the longitudinal channel;
a roller wheel disposed at least partially within the longitudinal channel and configured to engage the tubing, the roller wheel including a plurality of teeth extending from an outer surface of the roller wheel, wherein a longitudinal position of the roller wheel relative to the channel adjusts a flow rate through the tubing; and
a locking device releasably engaged to the housing and the roller wheel, wherein the locking device prevents movement of the roller wheel from the longitudinal position, the locking device comprising an immobilizer, the immobilizer including a plurality of locking teeth, wherein the locking teeth engage the housing and at least one of the plurality of teeth of the roller wheel to prevent movement of the roller wheel.

7. The roller clamp of claim 6, wherein the plurality of locking teeth engages at least one of a plurality of housing teeth of the housing.

8. The roller clamp of claim 6, wherein the roller wheel includes an axial lip defining the outer surface of the roller wheel.

9. The roller clamp of claim 8, wherein the immobilizer further comprises a first immobilizer wall and a second immobilizer wall, wherein the first immobilizer wall and the second immobilizer wall extend beyond the axial lip of the roller wheel.

10. The roller clamp of claim 9, wherein the first immobilizer wall defines a keyway.

11. A roller clamp, comprising:
a housing comprising a first wall and a second wall, wherein the first wall and the second wall are spaced apart to define a longitudinal channel therebetween, the housing including an upper opening and a lower opening configured to allow a tubing to pass through the longitudinal channel;
a roller wheel disposed at least partially within the longitudinal channel and configured to engage the tubing, the roller wheel including a plurality of teeth extending from an outer surface of the roller wheel, wherein a longitudinal position of the roller wheel relative to the channel adjusts a flow rate through the tubing; and
a locking device releasably engaged to the housing and the roller wheel, wherein the locking device prevents movement of the roller wheel from the longitudinal position,
wherein the first wall and the second wall are biased to contact the roller wheel, preventing movement of the roller wheel from the longitudinal position, and the locking device comprises a first wall extension of the first wall extending away from the roller wheel and a second wall extension of the second wall extending away from the roller wheel, wherein compressing the first wall extension and the second wall extension urge the first wall and the second wall away from the roller wheel to permit movement of the roller wheel from the longitudinal position.

12. A roller clamp, comprising:
a housing comprising a first wall and a second wall, wherein the first wall and the second wall are spaced apart to define a longitudinal channel therebetween, the housing including an upper opening and a lower opening configured to allow a tubing to pass through the longitudinal channel;
a roller wheel disposed at least partially within the longitudinal channel and configured to engage the tubing, the roller wheel including a plurality of teeth extending from an outer surface of the roller wheel, wherein a longitudinal position of the roller wheel relative to the channel adjusts a flow rate through the tubing; and
a locking device releasably engaged to the housing and the roller wheel, wherein the locking device prevents movement of the roller wheel from the longitudinal position, the locking device comprising a slider, the slider including a biasing arm engaging the roller wheel and configured to bias the roller wheel against the first wall.

* * * * *